United States Patent [19]
Yoshida

[11] 4,330,712
[45] May 18, 1982

[54] INSPECTION APPARATUS FOR DEFECTS ON PATTERNS

[75] Inventor: Hajime Yoshida, Tokyo, Japan
[73] Assignee: Hajime Industries Ltd., Tokyo, Japan
[21] Appl. No.: 116,450
[22] Filed: Jan. 29, 1980
[30] Foreign Application Priority Data Feb. 1, 1979 [JP] Japan .................................. 54-11100
Feb. 1, 1979 [JP] Japan .................................. 54-11101

[51] Int. Cl.³ ........................................... G01N 21/88
[52] U.S. Cl. ..................................... 250/572; 356/392
[58] Field of Search ............................... 356/388–394, 356/71; 250/571, 572, 562, 563, 556

[56] References Cited

U.S. PATENT DOCUMENTS

| | | | |
|---|---|---|---|
| 2,827,822 | 3/1958 | Timms | 356/71 |
| 3,411,007 | 11/1968 | Thompson | 356/388 |
| 3,560,093 | 2/1971 | Montone | 356/393 |
| 3,713,741 | 1/1973 | Sheehan | 356/392 |
| 3,778,166 | 12/1973 | Pease et al. | 356/390 |

*Primary Examiner*—David C. Nelms
*Attorney, Agent, or Firm*—Thomas R. Morrison

[57] ABSTRACT

An inspection apparatus for defects on patterns is disclosed which has a television camera picking up an object with a pattern to be inspected, an inspection device receiving an output from the television camera to inspect the object, an optical mask having a reference pattern made of opaque material and transparent material and serving as a reference for inspection of defects of the object, and a device for supporting the optical mask between the television camera and the object on the optical axis of the television camera in such a manner that the patterns of the object and optical mask are matched with each other on the optical axis of the television camera.

8 Claims, 5 Drawing Figures

INSPECTION APPARATUS FOR DEFECTS ON PATTERNS

BACKGROUND OF THE INVENTION

1. Field of the Invention

Present invention is related generally to a defect inspection apparatus for patterns which are used to detect the defects on patterns of the inspected subject.

2. Description of the Prior Art

Upon manufacturing semi-conductors or printed circuit boards, it is common that a photomask which contains a certain pattern is used. In such case, if there is a defect on the pattern of the photomask it will cause reject products and accordingly inspection for defects on the pattern of the photomask is an important process. A pattern defect inspection apparatus example based upon the prior art will be explained hereunder in reference with FIGS. 1, 2 and 3.

FIGS. 1 and 2 show a portion of a photomask as magnified by a microscope and on such drawings, 1 and 1' are photomasks of transparent material such as glass or the like, 2 and 2' show in general a pattern which is formed with, for example, evaporated metal or the like on photomasks 1 and 1', 3 is the transparent portion of the transparent base plate of photomasks 1 and 1', and 4 is the nontransparent or opaque portion by the evaporated material respectively. On FIG. 2, A and B are flaws formed by excess evaporated material unnecessarily remaining, and C and D are the portions where the necessary evaporated material is lacking. Accordingly, the photomask 1' which has the pattern 2' as shown on FIG. 2, is a defective product. On the other hand, the photomask 1 as shown on FIG. 1 is a complete normal product.

In order to inspect photomask 1 or 1' as shown on FIGS. 1 and 2 under the prior art, for instance, as shown on FIG. 3, a standard mask 6 which has a complete pattern (for instance as shown as pattern 2 on FIG. 1) is placed at a specified location on a transparent base 5. A mask 7 which is to be inspected (for instance, the defective mask such as shown on FIG. 2) is placed at another specified location on the base 5. Both masks are observed by a binocular microscope 8. On FIG. 3, 9 and 10 are the objective lenses for standard mask 6 as well as the inspected mask 7, 11 and 12 are the mirrors for both masks 6 and 7, in the same respect, 13 and 14 are the half mirrors for the masks 6 and 7, 15 is a common eye piece lens, 16 is the light source such as a red light which irradiates on standard mask 6 and 17 is another light source that irradiates a green light for instance which is the complimentary colour to red, which is irradiated on the inspected mask 7. Therefore, the lights that are irradiated from light sources 16 and 17 pass through the base 5, masks 6 and 7, lenses 9 and 10, mirrors 11 and 12, half mirrors 13 and 14, and further pass through lens 15 of the binocular microscope 8 to form an image at an observing eye 18, which makes the inspection of mask possible. When the inspected mask 7 is a defective product such as shown on FIG. 2, at portions A and B, the green light that is irradiated from light source 17 is shielded by portions A and B so that only the red light which is irradiated from light source 16 arrives at the observing eye 18, and hence these portions A and B appear red in colour. On the other hand, at portions C and D, the red light from light source 16 is shielded, and only the green light from light source 17 arrives at the observing eye 18, so that such portions C and D appear green in colour. For the other portions, which are the transparent section 3, the red and green lights as irradiated from light sources 16 and 17 respectively arrive at the observing eye 18 simultaneously and accordingly appear generally as white, and as for the nontransparent section 4, both of the red and green lights are shielded and do not pass which appears to be generally in black. In other words, when the entire view appears in white or black, there is no defect on the inspected mask 7, while when even a slight shade of red or green colour appears, the inspected mask 7 contains a defect.

The above described pattern inspection apparatus under the prior art has the fault that the inspected subject must be transparent and further since each piece must be inspected by human eyes, in order to automate this inspection process, an expensive colour television camera becomes necessary.

OBJECTS AND SUMMARY OF THE INVENTION

Therefore, it is an object of the present invention to provide a defect inspection apparatus for patterns which avoids the usage of an expensive colour television camera and which automatically conduct the inspection of defects on an inspected object using a low cost monochrome television camera.

According to an aspect of the present invention, an inspection apparatus for defects on patterns is provided which comprises:

(a) a television camera picking up an object with a pattern to be inspected;

(b) an inspection device receiving an output from said television camera to inspect said object;

(c) an optical mask having a reference pattern made of opaque material and transparent material and serving as a reference for inspection of defects of said object; and (d) means for supporting said optical mask between said television camera and said object on an optical axis of said television camera in such a manner that said patterns of said object and optical mask are matched with each other on said optical axis of said television camera.

The additional, and other objects, features and advantages of the present invention will become apparent from the following description taken in conjunction with accompanying drawings.

DESCRIPTION OF THE PREFERRED EMBODIMENTS

An example of the present invention with features as mentioned above will be explained hereunder in reference with FIG. 4.

Figure 1:
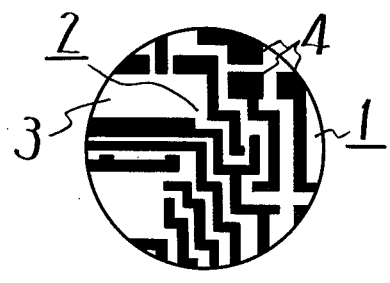
FIGS. 1, 2 and 3, respectively, are schematic diagrams which are illustrated to explain a defect inspection apparatus for patterns under the prior art.
Figure 2:
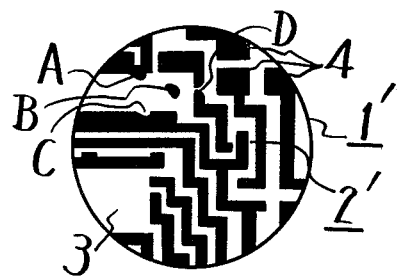
Figure 3:
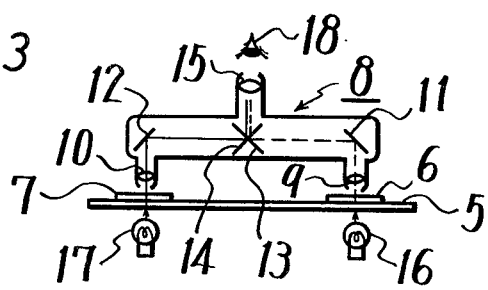
Figure 4:
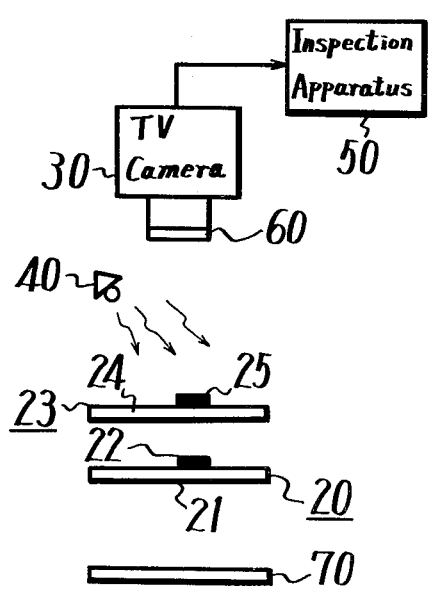
FIGS. 4 and 5 are schematic block diagrams which respectively show examples of the present invention.

On FIG. 4, 20 generally designates an object to be inspected such as a printed circuit board or the like, which consists of a base material or plate 21 and a pattern 22 formed on base plate 21 made by evaporating, for example, metal. Further, 23 generally designates a standard or reference subject or optical mask for the object to be inspected, which is constructed on a transparent base plate 24 such as glass, for instance, and a standard pattern 25 formed on the base plate 24 by evaporating material such as metal. In this case, while the colour of the material forming pattern 25 on the transparent base plate 24 of the optical mask 23 is selected to be the same as the colour of the base plate 21 of the object 20, it is necessary that this colour is different from the colour of the material that forms the pattern 22 on base plate 21.

In the case that the base material or plate 21 of the inspected object 20 is opaque, the inspection for defects such as "burr" or "whisker" of the pattern 22 which are surplus on the inspected object 20, will be explained hereunder.

First, the above mentioned pattern 22 on the base material 21 of the inspected object 20 and the pattern 25 on the transpatent base plate 24 of the standard subject 23 are placed so that both patterns 22 and 25 will be aligned on the light axis of a television camera 30, for instance, as shown in sequence on FIG. 4. A light source 40 is arranged as shown on the drawing, by which the standard subject 23 is irradiated from the side of television camera 30. Then, the standard subject 23 and object 20 are picked up by the television camera 30. Now, if it is assumed that the pattern 22 of the inspected object 20 is a complete product, the light that enters the television camera 30 is a light which is emitted from the light source 40, passes through the transparent base plate 24 of the standard subject 23 at portions where the nontransparent material or pattern 25 is not evaporated onto, is reflected from the surface of the base material 21 at portion where the pattern 22 to be inspected is not presented and again passes through the above mentioned transparent plate 24 to the television camera 30. The light from the light source 40 is also reflected from the surface of the material which forms pattern 25 (on FIG. 4, the inspected object 20 and the standard subject 23 are placed apart on the light axis of the television camera 30 at a distance, but in a practical application, both are generally in contact with each other). Accordingly, in the above case, the light that enters the television camera 30 is substantially limited to the light with the same colour only and hence the output from the television camera 30 becomes a uniform signal across the entire surface. Therefore, when the output from the television camera 30 is uniform over the entire surface, the inspected object 20 is a complete product.

However, if a surplus "burr" or "whisker" or the like defect exists at portions that form pattern 22 on base material 21 of the inspected object 20, the light from light source 40, other than the reflection from the surface of base material 21, is also reflected on such defect portion, and enters the television camera 30. As mentioned above, the colour of the material forming pattern 22 on the base material 21 is selected different to the colour of the material forming pattern 25 on the base material 24, so that whenever there is a defect such as a "burr" or "whisker", etc., on the pattern 22 to be inspected, the output signal from the television camera 30 is not uniform since different colours enters the television camera 30 and hence variation in the signal level is created at the portions corresponding to the defects. In other words, whenever there is a level change in the output signal of the television camera 30, the inspected object 20 is a defective product. Accordingly, if the output signal from the television camera 30 is supplied to an inspection apparatus 50 such as a differentiating circuit, level comparator or the like, defects in the inspected object can be discriminated.

In the drawing, 60 is an optical filter which is installed in front of the television camera 30, so that the defect portion may be increasingly distinctively discriminated from the surrounding portions.

When base material 21 of the inspected object 20 is transparent, if a reflection board 70 with the same colour as the material forming pattern 25 but with a different colour from the material forming pattern 22, is placed under the base material 21 of the inspected object 20 (on the drawing the base material 21 and the reflection board 70 are illustrated as placed apart, but in actual application can be generally in contact), in the same manner as above mentioned, the inspection of defects on the inspected object 20 by the television camera 30 may be conducted.

In this case, if, instead of installing the reflection board 70, the light source 40 may be placed under the inspected object 20 on the drawing, a similar inspection may be conducted.

Figure 5:
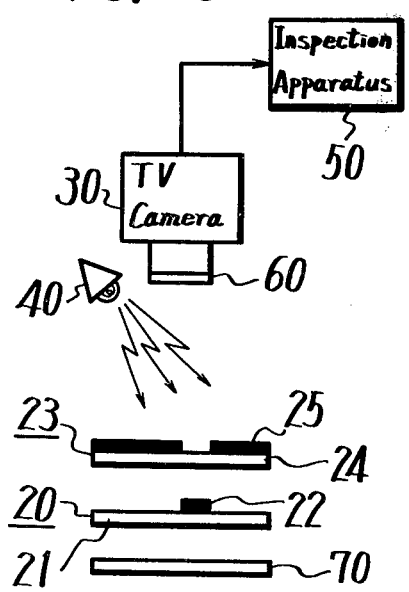

FIG. 5 shows another example of the present invention in which the same references as those used in FIG. 4 designate the same elements. In this example, the standard subject 23 for the inspected object 20 is also formed of a transparent base plate 24 such as glass or the like and the standard pattern 25. In this case, the optical characteristics of the standard pattern 25 are selected entirely opposite to those of the inspected subject pattern 22 on the base material 21 different to the example of FIG. 4. As an example case, at the corresponding portion on the transparent base plate 24, to the evaporated material pattern 22 (such as nontransparent or opaque material) on base plate 21, it is arranged so that the evaporated material for pattern 25 does not exist (accordingly, the corresponding portion on the transparent base plate 24 is transparent, and in other words the relation between the two is the same as a positive to a negative). Further, it is desirable that the colour of the material which forms pattern 22 on base plate 21 is selected to be the same colour as the material which forms pattern 25 on the transparent base plate 24, whereas it is necessary that the surface colour of the base material 21 on which the pattern 22 is formed be different to the former pattern material colour.

In case the base material 21 of the inspected object 20 is nontransparent or opaque, we shall explain about the inspection of defects such as cracks or openings in the object 20 by the example of the invention shown in FIG. 5. First, as above mentioned in connection with FIG. 4, the pattern 22 on the base material 21 of the inspected object 20 and the pattern 25 on the transparent base plate 24 of the standard subject 23 are placed so that both patterns 22 and 25 are in the same relation as a positive and negative, for instance, on the optical axis of the monochrome television camera 30 in sequence such as indicated on the drawing as an example. Then, the light source 40 is also arranged as shown on the drawing, by which the standard subject 23 is irradiated from the side of the television camera 30. Then, the standard subject 23 and so on will be picked up by the television camera 30. Now, if it is assumed that the pattern 22 of the inspected object 20 is a complete product, the light that enter the television camera 30 consists only of light which reflects from the nontransparent material of pattern 25 on transparent base plate 24 of the standard subject 23 light which passes through the transparent portions of the transparent base plate 24 where there is no material forming pattern 25, then reflects from the material forming pattern 22 on base material 21 and again passes through the transparent portion of base plate 24 to television camera 30 (FIG. 5 illustrates a space between the inspected object 20 and the standard subject 23 on the optical axis of the television camera 30, but in practical application, both plates are generally placed in contact with each other). Accordingly, the light that comes into the television camera 30 is generally light having a single colour and the output therefrom is a uniform signal from the entire surface. In other words, when the output from the television camera 30 is uniform over the entire inspected surface, the inspected object 20 is a complete product.

However, if there is a crack in pattern 22, an opening or the like as a defect on the material forming pattern 22 on base material 21 of the inspected object 20, the light from the light source 40 passes through such defective portion of the pattern 22 is reflected from base material 21 and enters the television camera 30. The surface colour of base material 21 of the object 20 is selected to be different from the colour of the material forming patterns 22 and 25, so that when there is a crack, an opening or the like on the inspected pattern 22, the output signal from the television camera 30 is not uniform and is disturbed in level at the portions corresponding to the defect. In other words, whenever there is a level change or variation in the output signal of the television camera 30, there is a defect on the inspected object 20. Therefore, if the output signal from the television camera 30 is supplied to the inspection apparatus 50, the goodness or badness of the inspected object can be discriminated similar to the example of FIG. 4.

In the above examples of the present invention, the optical mask or standard subject 23 is made of a transparent base plate 24 and a reference pattern 25 is coated or evaporated on the base plate 24, but an optical mask, which is made of transparent material and opaque material to form a plane reference pattern, can be of course used.

Further, while the light sources 40 in the above mentioned examples are placed at the side of the television camera 30, multiple light sources may be used or a half mirror or the like may be used to match the height axis of the light source and the optical axis of the television camera as may become necessary.

It is needless to say that although not indicated on the drawing, a drive means, which will hold the inspected object 20 as well as the standard subject 23 in the specified locations and to drive the same, is provided if necessary.

The above merely describes the preferred embodiments of the present invention and it is obvious that many variations or modifications could be effected by those skilled in the art without escaping the spirits or scope of the novel concepts of the present invention.

For instance, the surface colour of the base material 21 is selected the same colour as the material forming pattern 25 on the transparent base plate 24, while the color of the material forming pattern 22 is different in colour in the example of FIG. 4 and the colors of the materials forming the patterns 22 and 25 are selected same in the example of FIG. 5 but rather than limiting the above to the same colour or different colours, if the optical characteristics thereof are for instance, by the status of light reflection or absorption could be the same or different to obtain the same results.

It will be apparent that many modifications and variations could be effected by one skilled in the art without departing from the spirits or scope of the novel concepts of the present invention so that the spirits or scope of the invention should be determined by the appended claims only.

I claim as my invention:

1. Apparatus for inspecting an object having a pattern to be inspected on a base plate, said pattern to be inspected having a first colour and said base plate having a second different colour, comprising:

at least one mask including an opaque reference pattern on a transparent base plate;

said mask being positionable over said object with said reference pattern matched with one of said pattern to be inspected and portions of said base plate not covered by said pattern to be inspected and with the other thereof visible through portions of said transparent base plate not covered by said reference pattern;

said reference pattern having a colour the same as the portions of said object not covered by said reference pattern;

means for illuminating said mask and at least the portions of said object not covered by said reference pattern;

a monochrome television camera having a field of view encompassing said mask and the portions of said object not covered by said reference pattern; and means for detecting a discontinuity from a single colour in said field of view whereby errors in said pattern are detected.

2. Apparatus according to claim 1, further comprising an optical filter on said television camera, said optical filter being effective to enhance said discontinuity.

3. Apparatus according to claim 1, wherein said base plate of said object is transparent.

4. Apparatus according to claim 3, further comprising a reflection board at a side of said object remote from said television camera, said reflection board having the correct one of said first and second colours and contributing the correct one of said first and second colours to said base plate.

5. Apparatus according to claim 3, wherein said means for illuminating includes a first light source illuminating said reference pattern at the same side of said mask as said television camera and a second light source at a side of said object remote from said television camera, said second light source having a colour which imparts the correct one of said first and second colours to said base plate.

6. Apparatus according to claim 1, wherein said reference pattern is a positive replica of said pattern to be inspected and said reference pattern has said second colour.

7. Apparatus according to claim 1, wherein said reference pattern is a negative replica of said pattern to be inspected and said reference pattern has said first colour.

8. Apparatus according to claim 1, wherein said at least one mask includes a first mask having a first reference pattern, said first reference pattern being a positive replica of said pattern to be inspected and has said second colour and a second mask having a second reference pattern, said second reference pattern being a negative replica of said pattern to be inspected and has said first colour, said first and second masks being alternately usable on said object.

* * * * *